US008980807B2

(12) United States Patent
Hora et al.

(10) Patent No.: US 8,980,807 B2

(45) **Date of Patent: *Mar. 17, 2015**

(54) BLOWN AND STRIPPED BLEND OF SOYBEAN OIL AND CORN STILLAGE OIL

(75) Inventors: Michael John Hora, Marion, IA (US); Patrick Thomas Murphy, La Grange Park, IL (US); John Carl Tolfa, Midland, MI (US)

(73) Assignee: Cargill, Incorporated, Wayzata, MN (US)

( * ) Notice: Subject to any disclaimer, the term of this patent is extended or adjusted under 35 U.S.C. 154(b) by 37 days.

This patent is subject to a terminal disclaimer.

(21) Appl. No.: 13/699,059

(22) PCT Filed: May 20, 2011

(86) PCT No.: PCT/US2011/037359

§ 371 (c)(1), (2), (4) Date: Nov. 20, 2012

(87) PCT Pub. No.: WO2011/146848

PCT Pub. Date: Nov. 24, 2011

(65) Prior Publication Data

US 2013/0065803 A1 Mar. 14, 2013

Related U.S. Application Data

(60) Provisional application No. 61/347,192, filed on May 21, 2010.

(51) Int. Cl.

| | |
|---|---|
| ***C11B 3/16*** | (2006.01) |
| ***C07C 51/00*** | (2006.01) |
| ***C10M 101/04*** | (2006.01) |
| ***C11B 3/14*** | (2006.01) |
| ***C11B 3/00*** | (2006.01) |

(52) U.S. Cl.

CPC .. *C11B 3/14* (2013.01); *C11B 3/001* (2013.01)
USPC ............................ 508/459; 554/183; 554/167

(58) Field of Classification Search

CPC .................................. C11B 3/14; C11B 3/001
USPC ............ 554/183, 167; 585/240–242; 508/459
See application file for complete search history.

(56) References Cited

U.S. PATENT DOCUMENTS

| | | | | |
|---|---|---|---|---|
| 1,790,464 | A | 1/1931 | Adams et al. | |
| 2,569,124 | A | 9/1951 | Christenson et al. | |
| 2,657,224 | A | 10/1953 | Bierke | |
| 4,330,625 | A | 5/1982 | Miller et al. | |
| 4,552,775 | A | 11/1985 | Baeling et al. | |
| 4,589,990 | A | 5/1986 | Zehler et al. | |
| 4,650,598 | A | 3/1987 | Roberts et al. | |
| 5,512,313 | A | 4/1996 | Cooper et al. | |
| 6,312,826 | B1 | 11/2001 | Shogren | |
| 6,443,661 | B1 | 9/2002 | Wathen | |
| 6,589,442 | B1 | 7/2003 | Wilson et al. | |
| 6,759,542 | B2 * | 7/2004 | Mahlum | 554/183 |
| 6,822,105 | B1 | 11/2004 | Luxem et al. | |
| 7,262,311 | B2 * | 8/2007 | Christianson et al. | 554/183 |
| 7,601,858 | B2 | 10/2009 | Cantrell et al. | |
| 7,608,729 | B2 | 10/2009 | Winsness et al. | |
| 7,989,647 | B2 | 8/2011 | Geiger et al. | |
| 8,008,516 | B2 | 8/2011 | Cantrell et al. | |
| 8,580,988 | B2 * | 11/2013 | Hora et al. | 554/183 |
| 2004/0087808 | A1 | 5/2004 | Prevost et al. | |
| 2006/0107859 | A1 | 5/2006 | Sampei | |
| 2007/0004811 | A1 | 1/2007 | Bruner et al. | |
| 2007/0089356 | A1 | 4/2007 | Krasutsky et al. | |
| 2007/0260080 | A1 | 11/2007 | Lee et al. | |
| 2008/0190567 | A1 | 8/2008 | Winsness | |
| 2008/0299632 | A1 | 12/2008 | Winsness et al. | |
| 2009/0076913 | A1 | 3/2009 | Morgan | |
| 2009/0123609 | A1 | 5/2009 | Harris et al. | |
| 2009/0287007 | A1 | 11/2009 | Abraham et al. | |
| 2010/0036177 | A1 | 2/2010 | Ward | |
| 2011/0054098 | A1 | 3/2011 | Tutin et al. | |
| 2012/0065414 | A1 * | 3/2012 | Lochel | 554/9 |
| 2012/0065417 | A1 * | 3/2012 | Hora et al. | 554/124 |

FOREIGN PATENT DOCUMENTS

| | | | |
|---|---|---|---|
| WO | 0162880 | A1 | 8/2001 |
| WO | 2007088421 | A2 | 8/2007 |
| WO | 2010135637 | A1 | 11/2010 |

OTHER PUBLICATIONS

Edgar S. Lower, "Blown (air oxidised) vegetable & marine oils & paint manufacture," Pigment and Resin Technology, May 1987, pp. 7-10.

N. Singh & M. Cheryan, "Extraction of Oil From Corn Distillers Dried Grains with Solubles," Transactions of the ASAE, 1998 American Society of Agricultural Engineers, vol. 41, pp. 1775-1777.

* cited by examiner

*Primary Examiner* — Pamela H Weiss

(57) ABSTRACT

A method for producing a high viscosity, low volatiles blown stripped oil blend is provided. The method may include the steps of: (i) obtaining an oil blend of corn stillage oil and soybean oil having a weight ratio of corn stillage oil to soybean oil of from about 1:2 to 3:1; (ii) heating the oil blend to at least 90° C.; (iii) passing air through the heated oil blend to produce a blown oil having a viscosity of at least 50 cSt at 40° C.; and (iv) stripping the blown oil from step (iii) to reduce an acid value of the blown oil to less than 5.0 mg KOH/gram.

26 Claims, No Drawings

BLOWN AND STRIPPED BLEND OF SOYBEAN OIL AND CORN STILLAGE OIL

Cross Reference to Related Applications

This application is a section 371 national-stage phase of International Application No. PCT/US11/037359, filed 20 May 2011 entitled BLOWN AND STRIPPED BLEND OF SOYBEAN OIL AND CORN STILLAGE OIL, which claims priority to U.S. application Ser. No. 61/347,192, filed 21 May 2010 entitled BLOWN AND STRIPPED BLEND OF SOYBEAN OIL AND CORN STILLAGE OIL, which are hereby incorporated by reference in their entirety.

FIELD

The present disclosure relates to blown and stripped blends of soybean oil and corn stillage oil. The disclosure also relates to methods for making such oils

BACKGROUND

Lubricating and de-dusting oils historically have been made from petroleum feedstocks. These oils are typically designed for the application where they are to be utilized. Several of these applications require that the oil utilized be resistant to explosion and burning at high temperatures. Examples of applications where high temperature resistance is important include lubrication for metal forming processes, machine lubricants and de-dust oils for manufacturing processes, such as fiberglass insulation and stone wool insulation manufacturing.

Ethanol production from corn has increased in recent years. The corn is typically ground to a course powder that is then mixed with water and yeast and fermented to produce a fermented mixture (sometimes referred to as "mash") that contains residual solids, ethanol and other liquids. The other liquids include water, monoglycerides, diglycerides, triglycerides, glycerin, and free fatty acids. Typically, the liquid portion of the mash is heated to distill off the ethanol, which is captured and sold as an additive for automotive fuels.

The residual liquid remaining after the ethanol is removed contains free fatty acids and glycerol and from 1% to 3% by weight monoglycerides, diglycerides, triglycerides. The residual liquid from the distillation has generally been sold together with the solids portion of the mash as "distillers dry grain." The distillers dry grain generally is used as feed for livestock.

SUMMARY

In one embodiment, the invention comprises a method for making a high viscosity, low volatiles blown, stripped oil blend.

The oils used for the oil blend are corn stillage oil (as further described, below) and soybean oil. Typically, the weight ratio of corn stillage oil to soybean oil is from 1:2 to 3:1, preferably from 1:1 to 3:1, more preferably from 1:8:1 to 3:1, and more preferably from 1:8:1 to 2.5:1. The initial fatty acid content of the blend is from 4% to 9% by weight, preferably from 6% to 9%, more preferably from 8% to 9%, and more preferably from 8% to 8.6%.

When the oil blend is utilized to make a blown, stripped oil having a viscosity from 50 cSt to 200 cSt, preferably the weight ratio of corn stillage oil to soybean oil is from 2:1 to 3:1, preferably from 2.5:1 to 3:1.

In a first embodiment, the oil blend is blown for a sufficient period of time at an appropriate temperature to produce highly polymerized oil. For example, air is blown (sparged through) the oil blend being maintained at a temperature of from 90° C. to 125° C. (preferably from 100° to 120° C. and more preferably from 105° C. to 115° C.) typically for from 20 to 60 hours (preferably from 24 to 42 hours). The resulting polymerized oil blend is then relatively heavily stripped. During the stripping, the blown oil blend typically is heated to a temperature from 230° C. to 270° C. (preferably from 235° to 245° C.) and vacuum stripped at a pressure of 100 torr or less, preferably 75 torr or less, and more preferably 50 ton or less for typically from 10 to 40 hours (preferably from 20 to 30 hours).

Typically, the oil is stripped to reduce the fatty acid content of the oil blend until the acid value of the oil blend is less than 5 mg KOH/gram, preferably about 3.5 mg KOH/gram or less, and in some instances about 3.0 mg KOH/gram or less, and further about 2.8 mg KOH/gram or less. In some instances where a particularly low acid value is beneficial (for example lube oil compositions), the oil preferably is stripped until the acid value is 1.0 mg KOH/gram or less, preferably 0.5 mg KOH/gram or less. The final hydroxyl number of the blown, stripped oil blend is typically from 10 mg KOH/gram to 200 mg KOH/gram, preferably, the hydroxyl number of the blown, stripped oil blend typically is less than 50 mg KOH/gram, preferably less than 40 mg KOH/gram, and in some instances less than 30 mg KOH/gram, for example less than 25 mg KOH/gram.

The inventors have surprisingly found that the use of a polyol (for example glycerol) can optionally be utilized during the stripping to enhance the reduction of the fatty acid content of the blown, stripped oil blend to a desirably low level. The methods for using such a polyol are more fully described below.

The stripping reduces the content of free fatty acids and other volatiles. During the stripping process, the oil blend is also bodied. Typically, the final blown, stripped oil blend has a higher viscosity than the initial viscosity of the blown oil blend before stripping. The stripping also removes lower molecular weight glycerides and free fatty acids and unexpectedly can produce a blown stripped oil blend having a very high flash point. The blown, stripped oil blend can be used for end-use applications that require or take advantage of oils having high flash point. For example, the blown, stripped oil blends are particularly suitable for de-dusting fluids. "De-dusting fluids" are fluids used for reducing the dust created when a surface is agitated or perturbed. Examples of De-dusting fluids (De-dust oil) are oils that can be used to reduce the dust created during the manufacture of fiberglass and/or stone wool insulation. The stripped, blown oil blend will help minimize the chances of sparking and/or explosions in high temperature environments and will also degrade slower than petroleum based mineral oils having lower flash points. Typically, this blown, stripped oil blend has a flash point of at least 293° C., preferably at least 296° C., and more preferably at least 304° C., and in some instances at least 320° C. And, the blown, stripped oil blend typically has a viscosity at 40° C. or at least 60 cSt, preferably at least 300 cSt, more preferably at least 500 cSt and in some instances at least 700 cSt at 40° C. When high temperature operations are particularly important, the blown, stripped oil blend may have a viscosity of at least 2500 cSt at 40° C. and in some instances at least 5000 cSt at 40° C.

In a second embodiment, the oil blend is blown for a relatively shorter period of time to produce an oil blend that is lightly polymerized. For example, air is blown (sparged through) the oil blend being maintained at a temperature of from 90° C. to 125° C. (preferably from 100° to 120° C., and more preferably from 105° to 115° C.). typically for from 18 to 30 hours (preferably from 20 to 24 hours). The lightly polymerized oil is then relatively heavily stripped to reduce the content of free fatty acids and other volatiles within the oil. For example, the blown oil is heated to a temperature from 230° C. to 270° C. (preferably from 235° to 245° C.) and vacuum stripped at a pressure of 100 torr or less, preferably 75 torr or less, and more preferably 50 torr or less typically for from 8 to 12 hours (preferably from 9 to 11 hours). The resulting blown, stripped oil blend has a viscosity at 40° C. of from 50 cST to 200 cSt. This blown, stripped oil blend has an unexpectedly low pour point, typically less than −14° C. This low pour point oil is particularly useful for low temperature de-dust applications and for use in Bar & Chain lubricant end-use applications. Examples of end-use applications include many areas where petroleum based oils are used such as: chain saw lubricant applications and other applications that utilize bar, chain, and sprockets that demand medium viscosity oils to provide adequate lubrication. This blown, stripped oil blend can also be used in metal forming operations such as drawing, in hydraulic systems as a base fluid and in 2 cycle engine oil formulations. Examples of de-dust applications where relatively low pour points oils as described here are useful include: fertilizer plants where fertilizer is transferred outdoors in winter temperatures and rock crushing applications where dust is a concern. If a lower pour point is desired, additives such as a heavily blown linseed oil (such as the blown linseed oil available from Cargill, Incorporated under the trademark VOM 25), or diesters having a crystallization temperature less than −28.9° C., preferably less than −34° C., more preferably less than −40° C. and further more preferably less than −45° C. and in some instances less than −54° C. (such as bis(2-ethylhexyl)adipate) can be blended with the low pour point oil to produce a very low pour point oil having a pour point typically less than −23° C. and preferably less than −26° C.

For high temperature applications, such as those that require at least 293° C., and sometimes at least 296° C., for example at least 304° C., the weight loss of the blown, stripped oil blend when measured using thermal gravimetric analysis at a temperature of from about 293° C. to 304° C. for 25-35 minutes ("TGA") typically is less than 25 weight percent, preferably less than 20 weight percent and in some instances less than 15 weight percent. An example of the TGA procedures that can be used is the Noack Engine Oil Volatility (ASTM 5800-80) that has been modified for the appropriate temperature and duration as described below. The temperature and time utilized for measuring the weight loss of the blown, stripped oil should be adapted based on the predicted temperature profile that the oil will be exposed to in the end-use application. For example, if the oil will be exposed to temperatures of about 293° C. to 296° C. for a period of 50 minutes to 60 minutes, then the TGA typically would be carried out at or slightly above the highest predicted operating temperature of 296° C. (for example 298° C.) and for a sufficient time to predict the behavior of the oil at the end-use operating temperature (for example for a period of at least 45 minutes). The weight loss during the TGA is proportional to the amount of volatiles that may be liberated in the end-use application. The inventors have surprisingly found that the blown, stripped oil blends of the invention have much lower weight loss than typical petroleum-based oils under high temperature operating conditions.

DETAILED DESCRIPTION

"Flash Point" or "Flash Point Temperature" is a measure of the minimum temperature at which a material will initially flash with a brief flame. It is measured according to the method of ASTM D-92 using a Cleveland Open Cup and is reported in degrees Celsius (° C.).

"Pour Point" or "Pour Point Temperature" is a measure of the lowest temperature at which a fluid will flow. It is measured according to the method of ASTM D-97 and is reported in degrees Celsius (° C.).

"Iodine Value" (IV) is defined as the number of grams of iodine that will react with 100 grams of material being measure. Iodine value is a measure of the unsaturation (carbon-carbon double bonds and carbon-carbon triple bonds) present in a material. Iodine Value is reported in units of grams iodine ($I_2$) per 100 grams material and is determined using the procedure of AOCS Cd Id-92.

"Hydroxyl number" (OH#) is a measure of the hydroxyl (—OH) groups present in a material. It is reported in units of mg KOH/gram material and is measured according to the procedure of ASTM E1899-02.

"Acid Value" (AV) is a measure of the residual hydronium groups present in a compound and is reported in units of mg KOH/gram material. The acid number is measured according to the method of AOCS Cd 3d-63.

"Gardner Color Value" is a visual measure of the color of a material. It is determined according to the procedure of ASTM D1544, "Standard Test Method for Color of Transparent Liquids (Gardner Color Scale)". The Gardner Color scale ranges from colors of water-white to dark brown defined by a series of standards ranging from colorless to dark brown, against which the sample of interest is compared. Values range from 0 for the lightest to 18 for the darkest. For the purposes of the invention, the Gardner Color Value is measured on a sample of material at a temperature of 25° C.

Corn Stillage Oil and Soybean Oil Blends

The corn stillage oil and soybean oil are blended in the ratio described herein. The oils may be pre-blended prior to being introduced into the reactor where the blowing takes place, or they may be added separately to the reactor where the blowing takes place. The corn stillage oil has slightly high saturated carbon-carbon bonds and lower carbon-carbon double bonds than the soybean oil. Also, the corn stillage oil has lower polyunsaturated carbon-carbon bonds, such as triunsaturated carbon-carbon double bonds (18:3's) than soybean oil. When blown, corn stillage oil produces less hydroxyl groups per molecule than soybean oil. Therefore, for a blown oil having a given set of properties, a blown corn stillage oil typically will have a lower hydroxyl number than a blown soybean oil. When the blown, stripped oil blend needs to have a particularly low acid value (for example, an acid value of 3.0 mg KOH/gram or less), it may be advantageous to use higher amounts of soybean oil in the blend, so that more hydroxyl groups are available for reacting with free fatty acids present. However, a oil high in tri-unsaturated carbon-carbon bonds, such as soybean oil (which typically has about 7% 18:3 fatty acids) can produce more unwanted odor compounds during the blowing and stripping steps. Therefore, the percent of soybean oil should be maintained at acceptable levels. For blown, stripped oil blends, such as those having a viscosity from about 50 cSt to 200 cSt, this can be particularly important.

Preferably, refined, bleached, and deodorized (RBD) soybean oil is utilized in the invention. RBD soybean oil typically has an iodine value of from about 125-132 mg KOH/gram, an acid value of less than 1 mg KOH/gram (preferably less than 0.5 mg KOH/gram and more preferably less than 0.1 mg KOH/gram); and typically a hydroxyl number less than 1 mg KOH/gram.

Corn Stillage Oil

The inventors have surprisingly discovered that the monoglycerides, diglycerides, triglycerides, free fatty acids, and glycerol (hereinafter collectively referred to as "corn stillage oil") can be recovered from the other residual liquids resulting from the distillation of dry corn by suitable means, preferably by centrifugation of the residual material remaining after the ethanol has been distilled off. Centrifugation typically recovers twenty five percent of the corn stillage oil originally present in the residual material being centrifuged.

The corn stillage oil recovered by centrifugation typically: has an acid value from 16 to 32 mg KOH/gram, preferably from 18 to 30 mg KOH/gram; has an iodine value from 110 to 120 g $I_2$/100 g sample; and contains from 0.05 to 0.29 percent by weight monoglycerides, from 1.65-7.08 percent by weight diglycerides, from 70.00 to 86.84 percent by weight triglycerides, from 8 to 16 percent by weight (for example, from 9 to 15 percent by weight) free fatty acids, and from 0.00 to 0.20 weight percent glycerin. Typically, the corn stillage oil has from 53 to 55 percent by weight groups derived from diunsaturated fatty acids, from 39 to 43 percent by weight groups derived from monounsaturated fatty acids, from 15 to 18 percent by weight groups derived from saturated fatty acids, and from 1 to 2 percent by weight groups derived from triunsaturated fatty acids. The groups derived from each of the above fatty acids are present either as groups within the mono-, di-, and tri-glycerides or as free fatty acids.

The free fatty acid content of the corn stillage oil most commonly is from about 11 to 12 percent (an acid value of from about 22 to 24 mg KOH/gram) and is very high compared to conventional vegetable oils, including RBD soybean oil.

Recovery of corn Stillage Oil

Fermented mash comprising ethanol, water, residual grain solids (including proteins, fats, and unfermented sugars and carbohydrates), and from 1 to 3 percent by weight corn stillage oil is heated to distill and recover ethanol from the fermented mash.

After the ethanol is distilled off, the remaining liquid portion typically contains from 1 wt % to 4 wt % corn stillage oil. The material remaining after the ethanol is distilled off is typically centrifuged using a centrifuge, such as a Westfalia sliding disk centrifuge available from Westfalia Corporation. From 25 wt % to 35 wt % of the corn stillage oil contained in the material is recovered during this centrifugation step. The recovered unprocessed corn stillage oil typically exhibits a Gardner color of 12 or greater, for example, a Gardner color of from 14 to 18.

Unprocessed corn stillage oil typically exhibits: a viscosity at 40° C. of from 25 to 35 cSt (for example from 28 to 31 cSt) as measured utilizing viscosity tubes in a constant temperature bath as further described below; a viscosity at 100° C. of from 5 to 10 cSt for example from 6 to 9 cSt as measured utilizing viscosity tubes in a constant temperature bath as further described below; a Viscosity Index of from 80 to 236 determined using the procedures and measurement scale established by the Society of Automotive Engineers; a flash point from 220° C. to 245° C., for example from 225° C. to 240° C.; a saponification value of from 170 to 206 mg KOH/g; a pour point typically of from −5° C. to −14° C.; an acid value of from 15 to 33 mg KOH/gram (for example, from 16 to 32 mg KOH/gram); an iodine value from 110 to 125 grams $I_2$/100 grams sample; and from 8 to 16 wt % (for example, from 9 to 15 wt %) free fatty acids.

Viscosity for this invention is measured according to the method of ASTM D445. In this method oil to be tested is placed in a calibrated glass capillary viscometer, which is then placed into a constant temperature bath at the temperature specified. Once thermal equilibrium is reached, the oil is drawn up into the reservoir of the capillary tube. As the fluid drains, it passes the top mark on the tube and a timer is started. When the oil passes the lower mark, the timer is stopped and the flow time is recorded. The recorded flow time is multiplied by a factor which is specific to each viscometer tube. The resultant product of the flow time multiplied by the factor is reported as viscosity in cSt at the test temperature.

Unprocessed corn stillage oil also typically contains two phases at 25° C. The first phase is the liquid phase, which settles toward the top of any container that contains the corn stillage oil. This phase typically is reddish in color. The second phase is a solid that typically settles toward the bottom of any container containing the oil. At 62° C., the second phase tends to dissolve into the liquid phase, but will settle out again if the untreated corn stillage oil is cooled to room temperature. The inventors have determined that the second solid phase typically makes up at least 4 percent by weight (4 wt %) of the total unprocessed corn stillage oil. For example, the second solid phase may make up from 5 wt % to 12 wt % of the unprocessed corn stillage oil. For purposes of this invention, this second solid phase is referred to as the "titre."

Blowing the Oil Blend

The blowing typically is achieved by sparging air through the plant-based oil that has been heated to from 90° C. to 125° C., preferably from 100° C. to 120° C., and more preferably from 105° C. to 115° C. The vessel containing the plant-based oil during the blowing step typically is at atmospheric pressure. The pressure of the air being sparged through the oil is generally high enough to achieve the desired air flow through the plant-based oil. The air is introduced at a sufficient flow rate for a sufficient period of time to achieve the desired viscosity. Typically, the air is introduced into the plant-based oil at a rate of 0.009 to 0.011 cubic feet per minute per pound of oil present. Preferably, the air is dispersed evenly in the vessel to maximize surface area exposure. Typically the vessel will have a distribution ring or spoke-like header to create small volume bubbles evenly within the oil. The duration of sparging air through the oil is varied and determined according to the desired properties of the blown oil and the end-use applications for the resulting product.

Air is blown through the plant-based oil to provide blown-oil which advantageously has a relatively high level of polymerization, as shown by increased viscosities at 40° C. and 100° C. (typically above 50 cSt@40° C. preferably above 60 cSt@40° C. more preferably above 130 cSt@40° C., and further more preferably above 200 cSt@40° C., and in some instances where high molecular weight is particularly desirable, above 2500 cSt@40° C. and in some instances above 5000 cSt@40° C.

When corn stillage oil is blown without any additional oil being present, surprisingly, the acid value for the blown corn stillage oil is not significantly increased compared to the acid value for the unblown corn stillage oil. Typically the acid value remains the same or decreases when corn stillage oil is blown by itself For soybean oil blown by itself, the acid value is significantly increased when air is blown into the oil at temperatures above 100° C.

For blends of corn-stillage oil and soybean oils, the acid value will typically increase during the blow. Typically, for a blend of corn stillage oil and soybean oil having a weight ratio of corn stillage oil to soybean oil from about 1:2 to 3:1, the acid value after the blown blend has reached a viscosity of about 200 cSt at 40° C. is from about 7 to 10 mg KOH/gram for the 1:2 blend to about 13 to 16 mg KOH/gram for the 3:1 blend. The amount of increase will be proportional to the starting acid value of the blend and the ratio of corn stillage oil to soybean oil.

The reactions that occur during the blowing of the oil blend increase the molecular weight of the oil blend, which tends to increase the viscosity of the blown oil blend versus the unblown oil blend. Additionally, the blowing process introduces hydroxyl functionality onto the resulting oil, which also tends to increase the viscosity of the oil. The blown, oil blend typically has a hydroxyl number from 8 to 60 mg KOH/gram oil. As discussed earlier, the hydroxyl number of the blown oil blend will tend to increase as the percentage of soybean oil in the starting oil blend increases. The higher viscosity (especially at higher temperature) provides the oil with better hydrodynamic lubrication properties.

For high-flash point end-use applications (as described below) for example, high temperature de-dust applications, asphalt modifiers and open gear lubricants applications, the blowing is continued for a time sufficient to obtain a blown oil blend having a viscosity of: at least 200 cSt at 40° C., preferably at least 300 cSt at 40° C., and in some instances at least 1500 cSt at 40° C. This will provide for an oil blend having a viscosity of: at least 500 cSt at 40° C., preferably at least 700 cSt at 40° C., and more preferably at least 730 cSt at 40° C., and in some instances at least 5000 cSt at 40° C. after stripping (and bodying the oil) as described, below.

With even dispersion and small volume air bubbles, air typically is sparged through the oil blend for from 30 to 40 hours (when the oil blend is at a temperature of from 105° C. to 115° C. at atmospheric pressure, at the rates described above, to achieve these desired viscosities. Longer sparging times typically will be necessary if the air is not evenly dispersed within the oil and/or the volume of the air bubbles are relatively larger.

Optionally, a catalyst may be used in some embodiments to enhance the blowing of the oil. Examples of catalysts that may be useful include peroxides, and catalysts comprising metals selected from the group consisting of Transition Elements and Group IV metals as described in "McGraw-Hill Dictionary of Scientific and Technical Terms," Appendix 7 (Fifth Edition 1994).

Further examples of catalysts that may be useful for enhancing the blowing procedure include catalysts comprising metals related from the group consisting of: tin, cobalt, iron, zirconium, titanium and combinations thereof.

Stripping of the Oil Blend

The blown oil blend can be stripped using several methods. Examples of methods that may be utilized to strip the oil of unwanted volatile compounds include vacuum stripping and nitrogen stripping (where nitrogen is sparged through the oil).

Typically, the temperature during the stripping of the oil is from 230° C. to 270° C., preferably from 235° C. to 245° C. As discussed earlier, the stripping will body the oil and typically increase molecular weight and therefore raise the viscosity of the oil. The stripping will also lower the content of free fatty acids in the oil and therefore reduce the acid value of the resulting stripped oil.

In a first preferred aspect, the blown oil blend typically is stripped using vacuum stripping. During the vacuum stripping the pressure measured on a pipe in fluid communication with the head space of the reactor typically is less than 100 ton, preferably less than 75 torr, more preferably 50 ton or less, further more preferably less than 35 torr, and most preferably 20 ton or less. During vacuum stripping, the oil is typically lightly sparged with nitrogen gas to assist in the removal of volatiles. The nitrogen preferably is introduced at a rate high enough to assist in removal of the volatiles, but low enough to not prevent the pulling of the desired vacuum on the oil. Alternatively, the stripping may be conducted by applying a nitrogen sparge on the oil, without the use of a vacuum. If no vacuum is applied, the nitrogen preferably is sparged through the oil at a rate of from about 25 cfm to about 60 cfm through the oil per 45000 pounds mass of oil present. The stripping is continued until the desired acid value and viscosity are obtained.

In an alternative embodiment, the inventors have surprisingly discovered that when it is necessary to reduce the acid value to particularly low levels (for example to values of 3.5 mg KOH/gram or less), it may be advantageous to add small amounts of a polyol to the blown oil blend being stripped.

In a first preferred aspect of this alternative embodiment, the blown oil blend is stripped using nitrogen or vacuum stripping until the acid value of the oil is reduced to from 5 mg KOH/gram to about 9 mg KOH/gram, preferably from about 7 mg KOH/gram to about 9 mg KOH/gram. Then a polyol, preferably glycerin is added to the oil and the oil is stripped until the acid value of the oil is less than 5.0, preferably until the acid value is 3.5 mg KOH/gram or less, and in some instance 3.0 mg KOH/gram or less or 2.8 mg KOH/gram or less. During this final stripping stage, a nitrogen purge preferably is maintained on the oil to assist in the removal of volatiles from the oil, including water that may be liberated by the reaction of glycerin with fatty acids. However, during this final stripping state a vacuum preferably is no longer maintained on the vessel containing the oil. Once the acid value has been reduced to the desired value, the heat may be removed if the desired viscosity has been obtained. If the desired viscosity has not been reached, the oil will continue to be heated until the desired value for viscosity is obtained. After the desired acid value and viscosity have been obtained, the blown, stripped oil blend is allowed to cool. In this aspect the final hydroxyl number of the blown, stripped oil blend is typically less than 50 mg KOH/gram, preferably less than 40 mg KOH/gram, and in some instances less than 30 mg KOH/gram, for example from about 23 to 29 mg KOH/gram. If a higher viscosity oil is desired, the viscosity of the blown, stripped oil blend typically is at least about 500 cSt at 40° C., preferably at least 700 at 40° C., more preferably at least 730 cSt at 40° C., and in some instances at least 5000 cSt at 40° C. If a relatively lightly polymerized oil is desired, the viscosity of the blown, stripped oil blend is from 60 cSt to 200 cSt at 40° C.

The amount of polyol added to the blown oil blend in this first preferred aspect typically is sufficient to obtain a ratio of moles of hydroxyl groups added to fatty acid groups in the blown oil of from about 1:5 to less than about 1:1, preferably from about 1:4 to about 9:10, more preferably from about 2:5 to about 4:5; and further more preferably from 1:2 to 4:5.

In a second preferred aspect of this alternative embodiment, the polyol is added at the beginning or soon after stripping of the blown oil blend has commenced. In this second preferred aspect, the temperature of the blown oil blend is as described above. Typically, sufficient polyol (preferably glycerin) is added to the blown oil blend to obtain a ratio of moles of hydroxyl groups added per mole of fatty acids groups present in the oil of from about 1:1 to about 2:1, preferably from about 1.6:1 to about 1.9:1, and more preferably from about 1.75:1 to about 1.85:1. During this aspect, nitrogen is sparged through the oil, typically at a rate of from about 5 to 10 cfm per 45000 pounds mass oil. Preferably, during this aspect a vacuum is not applied to the oil. Nitrogen is sparged through the oil until the acid value of the oil is less than 5 mg KOH/gram, preferably less than 3.5 mg KOH/gram and in some instances 3.0 mg KOH/gram and even 2.8 mg KOH/gram. Once the acid value has been reduced to the desired value, the heat may be removed if the desired viscosity has been obtained. If the desired viscosity has not been reached, the oil will continue to be heated until the desired value for viscosity is obtained. After the desired acid value and viscosity have been obtained, the blown, stripped oil blend is allowed to cool. If a higher viscosity oil is desired, the viscosity of the blown, stripped oil blend typically is at least about 500 cSt at 40° C., preferably at least 700 at 40° C., more preferably at least 730 cSt at 40° C., and in some instances at least 5000 cSt at 40° C. If a relatively lightly polymerized oil is desired, the viscosity of the blown, stripped oil blend is from 60 cSt to 200 cSt at 40° C.

Stripping the oil increases the viscosity of the resulting oil compared to the non-stripped oil and will increase the flash point of resulting oil. If no glycerin is added to assist the stripping, it typically takes from about 20 to 30 hours (preferably from 24 to 27 hours) to obtain an acid value of less than 5.0 mg KOH/gram and a viscosity of at least 500 cSt at 40° C. (preferably an acid value of about 3.5 mg KOH/gram or less and a viscosity of at least 520 cSt at 40° C.). If the first aspect described above for adding a polyol is utilized, it typically takes a stripping time from about 12 to about 20 hours (preferably from about 14 to about 18 hours) to obtain a blown, stripped oil blend having the properties described. If the second aspect described above is utilized for adding a polyol, it typically takes a stripping time of from about 10 to about 14 hours (preferably from about 11 to about 13 hours) to obtain a blown, stripped oil blend having the properties described above.

In both aspects of the alternative embodiment, surprisingly, the addition of the polyol to the blown oil blend does not adversely affect the properties of the blown stripped oil blend; and a blown stripped oil blend having a high viscosity and high flash point is produced.

Polyol

As discussed above, the inventors have surprisingly discovered that by operationally adding a polyol to the blown oil blend, the blown oil blend may be more readily stripped to obtain a blown, stripped blends and in particular blends having high viscosites (for examples at least 500 cSt at 40° C., preferably at least 520 cSt at 40° C.) and a low acid value as described above, which will result in a blown, stripped oil blend having a high flash point.

The added polyol preferably has a molecular weight of at least 80 Daltons, more preferably at least 85 Daltons, and more preferably at least 90 Daltons. In order to aid in the reaction of the polyol with the free fatty acids, the polyol preferably has a hydroxyl number of at least 200 mg KOH/gram, more preferably at least 1000 mg KOH/gram. Preferably, the polyol has at least two hydroxyl groups per molecule, and more preferably at least 3 hydroxyl groups per molecule. The polyol preferably has a boiling point of at least 250° C., more preferably at least 270° C., and further more preferably at least 285° C. Any reference to boiling point herein means the boiling point at a pressure of 760 mm Hg. Due to its relatively high molecular weight (92 Daltons), relatively high boiling point (290° C.), high number of hydroxyl groups per molecule (3), and ready commercial availability, glycerin is the preferred polyol to utilize in the invention.

Examples of other polyols that may be utilized include, but are not limited to, trimethylol propane ("TMP"), polyethylene glycol ("PEG"), pentaerythritol, and polyglycerol.

In certain preferred aspects of the invention, the polyol (e.g. glycerol) contains less than 500 ppm chloride ions. In certain aspects, the polyol contains less than 300 ppm, less than 200 ppm, less than 100 ppm, less than 70 ppm, or less than 50 ppm chloride ions. Reduced chloride ion concentrations may minimize corrosion concerns in products that are manufactured utilizing a blown, stripped plant-based oil of the present invention. In one particularly preferred aspect, the polyol comprises technical grade or USP glycerol, typically having less than 30 ppm chloride ions and preferably less than 20 ppm chloride ions (for example less than 10 ppm chloride ions).

End-Use Applications

High-Flash Point Applications

High flash point applications often expose lubricating oil to temperatures above 500° F., often above 550° F. and in some instance temperature up to and/or above 600° F. Petroleum-based oils generally do not have flash point temperatures high enough to safely operate in this type of environments. Also, the petroleum-based oils may break down and rapidly oxidize and in a worst case scenario may burn in these types of environments. The inventors have surprisingly found that by heavily blowing an oil blend as described herein, the molecular weight and viscosity can be increased sufficiently to be able to operate effectively in end-use applications requiring such high flash points once the resulting blown has been stripped to reduce the acid value to 3.5 mg KOH/g or less, preferably 3.0 mg KOH/g or less, and more preferably 2.8 mg KOH/g or less.

Examples of suitable applications for the blown, stripped oil blend of the invention include De-dusting fluids that require a flash point of at least 293° C., preferably at least 296° C., and more preferably at least 304° C., and in some instances at least 320° C.

The blown, stripped oil blend will help minimize the chances of sparking and/or explosions in high flash point environments and will also degrade slower than petroleum based mineral oils having lower flash points.

Typically, the high-flash point blown, stripped oil blend typically also exhibits a pour point of lower than 0° C., preferably lower than negative 5° C. This combination of high flash point and relatively low pour point is unexpected and is believed to result from the blown, stripped oil blend having a relatively narrow molecular weight distribution with completely randomized molecular structures compared to petroleum base oils. This provides an oil that remains flowable at relatively low temperatures, while still exhibiting good viscosity and lubrication at high temperatures and a high flash point, as described above.

Examples of additional end-use applications that require such high flash points oils include, but are not limited to, asphalt modification, metal forging lubricants, fluids for stabilization of sand molds utilized in metal casting, and high temperature bearing lubricants. Examples of applications where the blown, stripped oil blends of this invention are advantageous include applications where high temperature De-dusting fluids are utilized, such as in the manufacture of fiberglass insulation and stone wool insulation applications.

EXAMPLES

The following examples are presented to illustrate the present invention and to assist one of ordinary skill in making and using the same. The examples are not intended in any way to otherwise limit the scope of the invention.

Example 1

Production of Vacuum Distilled Corn Stillage Oil

The vacuum distilled corn stillage oil of example 1 is made according to the ICM Process. This process exposes the fermented corn mash to temperatures of about 82.2° C. under a vacuum from about 50 to about 300 ton to distill off ethanol. The corn stillage oil is recovered by centrifuging the materials remaining after the distillation to recover the vacuum distilled corn stillage oil. The properties of the vacuum distilled corn stillage oil is set forth below in Table 2. While not measured, the vacuum distilled corn stillage oil is believed to contain from about 5 to about 12 percent by weight titre.

TABLE 2

Properties of Vacuum Distilled Corn Stillage Oil

| | Sample No. 2-1 |
|---|---|
| 40° C. Viscosity (cSt) | 31 |
| 100° Viscosity (cSt) | 8 |
| Viscosity Index | 249 |
| Flash Point (° C.) | 238 |
| Saponification Value (mg KOH/g) | 202 |
| Pour Point Temperature (° C.) | −7 |
| Acid Value (mg KOH/grams) | 22.2 |
| Free Fatty Acid (wt %) | 11.1 |
| Iodine value (gram $I_2$/100 grams) | 122 |
| Gardner Color | 15 |
| Hydroxyl number (mg KOH/gram) | 9 |

Example 1a

Production of Pressure Distilled Corm Stillage Oil

The pressure distilled corn stillage oil of example la is made according to the Delta T Process. In this process the fermented corn mash is exposed to temperatures of about 235° F. to 250° F. at pressures of from about 1 psig to about 15 psig to distill off ethanol. The pressure distilled corn stillage oil is recovered by centrifuging the material remaining after the distillation to recover the pressure distilled corn stillage oil. The properties of the pressure distilled corn stillage oil is set forth below in Table 2a. While not measured, the pressure distilled corn stillage oil is believed to contain from about 5 to about 12 percent by weight titre.

TABLE 2a

Properties of Pressure Distilled Corn Stillage Oils

| | Sample No. 2-1a |
|---|---|
| 40° C. Viscosity (cSt) | 31 |
| 100° Viscosity (cSt) | 8 |
| Viscosity Index | 249 |
| Flash Point (° C.) | 238 |
| Saponification Value (mg KOH/g) | 202 |
| Pour Point Temperature (° C.) | −7 |
| Acid Value (mg KOH/gram) | 23 |
| Free Fatty Acid (wt %) | 11.5 |
| Iodine value (gram $I_2$/100 grams) | 118 |
| Gardner Color | 16 |
| Hydroxyl number (mg KOH/gram) | 9 |

Example 2

Blowing the Corn Stillage Oil and Soybean Oil Blend

Into a 6000 gallon steel tank equipped with an air sparge distributor, positive displacement blower, regenerative thermal oxidizer(RTO) system, controlled heat source(whether it be external steam or hot oil jacket), and cooling coils, 45,000 pounds of corn stillage oil and soybean oil blend, as indicated in Table 3, is charged. The corn stillage oil utilized is similar to the corn stillage oil of Sample 2-1. The soybean oil is refined, bleached, and deodorized (RBD) soybean oil having an acid value of less than 0.5 mg KOH/gram. Air is sparged through the oil blend as it is heated to the temperature indicated in Table 3. The air is sparged through the oil blend at a rate that maximizes the rate while at the same time causes a relatively even distribution of air bubbles within the oil. The rate of sparging is set so the reactor remains under a slight vacuum which indicates the RTO system can remove VOCs adequately and safely as they are produced from the reaction. The speed with which viscosity increases is directly proportional to the rate at which air is being blown into the corn stillage oil, and indirectly proportional to the size of the air bubbles. The smaller the air bubbles, the more surface area the faster the reaction. The oil within the reactor is tested periodically to determine the viscosity at 40° C. of the blown oil. When the desired viscosity is obtained, the air sparging is stopped and the reactor is allowed to cool. Air is sparged through each of the samples for the times indicated in Table 3.

The properties of the resulting blown oil blends are set forth below in Table 3.

TABLE 3

Properties of Blown Corn Stillage Oil and soybean oil blend

| | Sample No. | | |
|---|---|---|---|
| | 3-1 | 3-2 | 3-3 |
| Corn Stillage Oil:soybean oil ratio | 2:3 | 2:1 | 4:1 |
| Sparging Temperature (° C.) | 115 | 115 | 115 |
| Sparging Time (hours) | 51 | 44 | 42 |
| Viscosity@40° C. (cSt) | 200 | 237 | 192 |
| Acid Value (mg KOH/gram) | 8 | 14 | 17 |
| Free Fatty Acid (wt %) | 4 | 7 | 8.5 |
| Gardner Color | 7 | 7 | 7 |
| Hydroxyl number (mg KOH/gram) | 28 | 52 | 30 |

As can be seen from Table 3, varying the weight ratio of corn stillage oil to soybean oil results in blown oil blends having varying properties, such as viscosity, for an approximately equal blowing time. Also, it can be seen from Table 2 that oil blends having higher corn stillage oil to soybean oil ratios (i.e. higher relative percentage of corn stillage oil) will take shorter blowing times periods to reach a given viscosity (or alternatively will reach a higher viscosity during the same time period) than blends having lower relative percentages of corn stillage oil.

In addition, while not measured, the blown oil blends of Table 3 are believed to contain less than one percent by weight titre.

Example 3

Stripping the Blown, Stripped Oil Blend

Into a 6000 gallon stainless steel reactor equipped with a mechanical agitator, a nitrogen sparge distributor, vacuum pump, regenerative thermal oxidizer(RTO) system, controlled heat source(hot oil jacket), cooling coils, and an overhead surface condenser, 45,000 pounds of blown corn stillage and soybean oil from example 2, as indicated by the ratios in Table 4, is charged. Nitrogen is sparged at about 5-10 CFM through the oil as it is heated to a temperature of from 235° C. to 245° C. Once the oil reaches the desired temperature, shut off nitrogen sparge and apply full vacuum to the reactor to the lower the pressure to 20 torr or less as measured on the vapor duct between the reactor and surface condenser. The oil within the reactor is tested periodically to determine the viscosity at 40° C., flash point, and the acid value of the oil. When the oil reaches acid value 7-9 mg KOH/gram, break the vacuum to atmospheric pressure. Add desired amount of glycerol to the oil in the reactor and continue to sparge with nitrogen to strip the reactor while maintaining the oil at 235° C. to 245° C. and atmospheric pressure until acid value is less than 5.0 and preferably less than 3.5 mg KOH/gram. When the desired viscosity, flash point, and acid value are obtained, cool the reactor. The oil samples are reacted for the times indicated in Table 4. The properties of the resulting stripped oils are set forth in Table 4.

TABLE 4

Properties of Stripped Blown Corn Stillage and Soybean Oil Blend

| | Sample No. | | | | |
|---|---|---|---|---|---|
| | 4-1 | 4-2 | 4-3 | 4-4 | 4-5 |
| Sample No. of blown, oil blend | 3-1 | * | 3-2 | 3-3 | 3-3 |
| utilized Polyol Added (% wt) | 0 | 1.2% | 0 | 0 | 0.15% |
| Molar ratio of OH-groups added to fatty acids present | N/A | 1.8:1 | N/A | N/A | 0.77:1 |
| Glycerol Hydroxyl number (mg KOH/gram) | N/A | 1800 | N/A | N/A | 1800 |
| Reaction time (hours) | 27 | 20 | 29 | 40 | 27 |
| Acid Value (mg KOH/gram) | 3.5 | 2.2 | 3.0 | 3.9 | 2.7 |
| Hydroxyl number (mg KOH/gram) | 34 | 37 | 30 | | 19 |
| Flash Point COC ° C. | 313 | 316 | 305 | 306 | 326 |
| Viscosity @ 40° C. (cSt) | 521 | 531 | 550 | 512 | 465 |

*The blown oil blend utilized to make Sample No. 4-2 is made by a procedure similar to the procedure of Example 2. The corn stillage oil to soybean ratio of the blend is 2:3. The blown oil blend had a viscosity of about 200 cSt @ 40° C., an acid value of 8 mg KOH/gram, a free fatty acid content of 4 wt %, a Gardner color of 7, and a hydroxyl number of about 30 mg KOH/gram.

Various Blown, Stripped Oil Blends are manufactured using procedures similar to the procedures similar to the procedures described for Examples 2 and 3, above. The initial weight ratio of corn still oil and soybean oil in the blend before blowing and stripping are set forth in Table 5. The final viscosity, OH# and acid value are also shown. As can be seen from Table 5, a blown, stripped oil blend having a viscosity of from 480 to 550 cSt at 40° C. can be manufactured faster using a starting oil blend having from 2:1 to 3:1 and preferably from 2:1 to 2.5:1 than blends having corn stillage oil to soybean oil ratios less than 2:1 and greater than 3:1.

TABLE 5

| Corn Stillage Oil:Soybean Oil Weight Ratio | Blowing Time (hours) | Stripping Time (hours) | Viscosity@40° C. (cSt) | OH-Number (mg KOH/gram) | Total Time (hours) | Final Acid Value (mg KOH/gram) |
|---|---|---|---|---|---|---|
| 42:58 | 51 | 27 | 513 | 25 | 78 | 3.5 |
| 67:33 | 44 | 29 | 541 | 39 | 73 | 3.5 |
| 80:20 | 42 | 40 | 546 | | 82 | 3.7 |
| 98:2 | 40 | 53 | 488 | 10 | 93 | 5.1* |

*Were not able to reduce the acid value below 5.0 with only vacuum

What is claimed is:

1. A method for producing a high viscosity, low volatiles blown stripped oil blend, the method comprising the steps of:

(a) obtaining an oil blend of corn stillage oil and soybean oil having a weight ratio of corn stillage oil to soybean oil of from about 1:2 to 3:1;

(b) heating the oil blend to at least 90° C.;

(c) passing air through the heated oil blend to produce a blown oil having a viscosity of at least 50 cSt at 40° C.; and (d) stripping the blown oil from step (c) reduce an acid value of the blown oil to less than 5.0 mg KOH/gram;

wherein the oil resulting from step (d) exhibits a viscosity of at least 60 cSt at 40° C. and a flash point of at least 290° C.

2. The method of claim 1 wherein the oil sulting from step (d) exhibits a viscosity of at least 500 cSt at 40° C.

3. The method of claim 1, wherein the oil resulting from step (d) exhibits: a viscosity of at least 5000 cSt at 40° C.

4. The method of claim 1, wherein the oil resulting from step (d) exhibits an acid value of 3.5 mg KOHI/gam or less.

5. The method of claim 1, wherein the oil resulting from step (d) exhibits a flash point of at least 295° C.

6. The method of claim 1, wherein the oil resulting from step (d) exhibits: a viscosity at 40° C. of at least 700 cSt; a viscosity at 100° C. of at least 63 cSt; an acid value of 3.5 mg KOH/gram or less; a hydroxyl number of from 10 to 30; and a flash point of at least 310° C.

7. The method of claim 1, wherein the weight ratio of corn stillage oil to soybean oil is from 1:1 to 3:1.

8. The method of claim 1, wherein an initial acid value of the oil blend of step (a) is from 12 mg KOH/gram to 18 mg KOH/gram.

9. The method of claim 1, wherein the oil resulting from step (d) exhibits:

a viscosity at 40° C. of at least 730 cSt; a viscosity at 100° C. of at least 68 cSt; an acid value of 3.0 mg KOH/gram or less; and a flash point of at least 315° C.; and a hydroxyl number of less than 25 mg KOH/mg.

10. The method of claim 1, wherein the oil resulting from step (d) exhibits a flash point of at least 320° C.

11. The method of claim 1, wherein, the oil resulting from step (d) exhibits an acid value of 2.8 mg KOH/gram or less.

12. The method of claim 1, wherein the weight ratio of corn. stillage oil to soybean oil is from 2:1 to 3:1.

13. The method of claim 12, wherein an initial acid value of the oil blend of step (a) is from 16 mg KOH/gam to 18 mg KOH/gram.

14. The method of claim 1, wherein a catalyst comprising a metal selected from the groups consisting of Transition Elements and Group IV is added to the oil prior to or during step (c).

15. The method of claim 1, wherein a catalyst is added to the oil prior to or during step (c), the catalyst comprising a metal selected from the group consisting of: tin, cobalt, iron, zirconium, titanium, and combinations thereof.

16. A method for producing a high viscosity, low volatiles blown, stripped oil blend, the method comprising the steps of:

(a) obtaining an oil blend of corn. stillage oil and soybean oil having a we ratio of corn stillage oil to soybean oil of from 1:2 to 3:1, the oil blend having an initial acid value of from 8 mg KOH/gram to 18 mg KOH/gram;

(b) heating the oil blend to at least 90° C.;

(c) passing air through the heated oil blend to produce a blown oil blend;

(d) stripping the blown oil blend to reduce the acid value of the blown oil blend to from 5 mg KOH/gram to 9 m.g KOH/gram;

(e) adding a sufficient amount of glycerin to the stripped blown oil from (d) to obtain a molar ratio of hydroxyl groups from the added glycerin to the free fatty acids present in the oil from (d) of from 1:5 to less than 1:1; and (f) stripping the oil from step (e) to a final acid value of 3.5 mg KOH/gram or less.

17. The method of claim 16, wherein sufficient glycerin is added to obtain a molar ratio of hydroxyl groups from the added glycerin to the free fatty acids present in the oil from (d) of from 1:5 to 8:10.

18. The method of claim 17, wherein the initial acid value of the oil blend of (a) is from 14 mg KOH/gram to 17 mg KOH/gram.

19. The method of claim 16, wherein the oil resulting from step (f) has a flash point of at least 293° C.

20. The method of claim 16, wherein, the oil resulting from step (f) has a flash point of at least 310° C. and exhibits a viscosity of at least 680 cSt at 40° C. and a viscosity of at least 63 cSt at 100° C.

21. The method of claim 16, wherein the oil from step (f) has a flash point of at least 315° C.

22. The method of claim 16, wherein the oil from step (f) has an acid value of 3.0 mg KOH/gram or less.

23. The method of claim 16, wherein he oil from step (f) has an acid value of 3.0 mg KOH/gram.

24. The method of claim 1, wherein the blown,stripped oil blend has a viscosity of at least 5000 cSt at 40° C.

25. The method of claim 1, wherein the oil resulting from step (d) exhibits an acid value of 3.0 mg KOH/gram or less.

26. A method for producing a high viscosity, low volatiles blown stripped oil blend, the method comprising the steps of:

(e) obtaining an oil blend of corn stillage oil and soybean oil having a weight ratio of corn stillage oil to soybean oil of from about 1:2 to 3:1;

(f) heating the oil blend to at least 90° C.;

(g) passing air through the heated oil blend to produce a blown oil having a viscosity of at least 50 cSt at 40° C.; and (h) stripping the blown oil from step (c) to reduce an acid value of the blown oil to less than 5.0 mg KOH/gram;

wherein the oil resulting from step (d) exhibits a viscosity of 550 cSt at 40° C. or less and a flash point of at least 290° C.

* * * * *

UNITED STATES PATENT AND TRADEMARK OFFICE

CERTIFICATE OF CORRECTION

PATENT NO. : 8,980,807 B2
APPLICATION NO. : 13/699059
DATED : March 17, 2015
INVENTOR(S) : Michael John Hora et al.

It is certified that error appears in the above-identified patent and that said Letters Patent is hereby corrected as shown below:

In the Specification

In column 8, line 8, delete “50 ton” and insert -- 50 torr --, therefor.

In column 8, line 10, delete “20 ton” and insert -- 20 torr --, therefor.

In the Claims

In column 15, line 1, in claim 1, after “step (c)” insert -- to --.

In column 15, line 6, in claim 2, delete “sulting” and insert -- resulting --, therefor.

In column 15, line 11, in claim 4, delete “KOHI/gam” and insert -- KOH/gram --, therefor.

In column 15, line 37, in claim 13, delete “KOH/gam” and insert -- KOH/gram --, therefor.

In column 15, line 50, in claim 16, delete “we” and insert -- weight --, therefor.

In column 16, lines 31-32, in claim 23, delete “wherein he oil from step (f) has an acid value of 3.0 mg KOH/gram.” and insert -- wherein the oil from step (f) has a hydroxyl number less than 50 mg KOH/gram. --, therefor.

Signed and Sealed this
Eighteenth Day of August, 2015

Michelle K. Lee
*Director of the United States Patent and Trademark Office*